US005446775A

United States Patent [19]
Wright et al.

[11] Patent Number: 5,446,775
[45] Date of Patent: Aug. 29, 1995

[54] MOTION DETECTOR AND COUNTER

[76] Inventors: Larry A. Wright, 1413 SE. 8th Ave., Okeechobee, Fla. 34974; Al Muldoon, 2603 Willa Dr., St. Joe, Mich. 49085

[21] Appl. No.: 169,640

[22] Filed: Dec. 20, 1993

[51] Int. Cl.6 .................. A63B 71/06; G01P 1/07
[52] U.S. Cl. .................... 377/24.2; 377/5; 377/23
[58] Field of Search .................. 377/5, 23, 24.2

[56] References Cited

U.S. PATENT DOCUMENTS

| | | | |
|---|---|---|---|
| 4,852,875 | 8/1989 | McLennan et al. | 377/23 |
| 5,294,913 | 3/1994 | Mower et al. | 377/5 |

*Primary Examiner*—Margaret Rose Wambach
*Attorney, Agent, or Firm*—Jacobson, Price, Holman & Stern

[57] ABSTRACT

A device for detecting and counting occurrences of specific human motions. The device includes structure for mounting the device to an object or a part of the human body which takes part in the motion. The device further comprises at least one acceleration-sensitive switch, a computer connected to an output from the acceleration-sensitive switch, a reset switch connected to the computer, and a display which is controlled by the computer. The acceleration-sensitive switch is preferably uniaxial, and therefore closes to complete a circuit and generates a pulse only when subjected to acceleration forces in a predetermined direction. The computer is programmed to detect the duration of the pulses received from the acceleration-sensitive switch, and is further programmed with parameters indicative of the minimum duration of such a pulse which will be deemed to have resulted from the occurrence of the specific human motion. By programming the computer in this manner, the computer determines when the human motion has occurred. The computer is further programmed to count the number of pulses which have exceeded the minimum duration, and to generate an output signal to the display indicative of this count.

10 Claims, 5 Drawing Sheets

MOTION DETECTOR AND COUNTER

BACKGROUND OF THE INVENTION

1. Field of the Invention

The present invention relates to a device for detecting and counting occurrences of specific human motions. The device finds particular usefulness in counting the number of times a fishing line is cast. Other uses of the device, for example, include counting pitches, or swings of a bat, racket or club.

2. Prior Art

A commonly known device for measuring human activity is the pedometer which measures how far a person walks. While pedometers do not actually display the number of steps a person takes, they do detect individual steps and increment a distance measurement in response to each step.

Though pedometers are generally effective, they suffer from several drawbacks. In particular, these devices trigger and increment the distance measurement in response to a wide range of motions other than walking. Because these other motions trigger the device, the resulting distance measurement is not necessarily accurate. Pedometers also can be triggered repeatedly by the same occurrence of a motion thus further diminishing the accuracy of the distance measurement.

Other devices for measuring activity include odometers which measure distance traveled and assembly line mechanisms which count the number of goods produced by an assembly line. Though these devices can provide accurate distance measurements and counting, they typically require an external frame of reference and measure only those motions that are identical at each occurrence.

SUMMARY OF THE INVENTION

It is a primary object of the present invention to provide a device capable of counting occurrences of a specific human activity or motion such as pitching, casting of a fishing rod, throwing, etc.

A further object of the present invention is to provide a self-contained device having no external frame of reference and capable of counting occurrences of the specific human activity or motion at any location including motions occurring in the outdoors.

Yet another object of the present invention is to provide a device capable of counting occurrences of the specific human activity, even if the motions which make up the activity are not exactly identical each time the activity is carried out.

Another object of the present invention is to provide a device which automatically ignores random bumps or movements which do not correspond to the human activity being counted.

To achieve these and other objects, the present invention comprises a device for detecting and counting occurrences of specific human motions. The device includes means for mounting the device to a part of the human body which takes part in the motion. The means for mounting, for example, engages a wrist or hand, or alternatively, engages an extension of the human body such as a fishing rod or a racket. Alternatively, the device can be built into a fishing rod or other extensions, such as a tennis racket.

The device further comprises an acceleration-sensitive switch, a computer connected to an output from the acceleration-sensitive switch, a reset switch connected to the computer, and a display which is controlled by the computer.

The acceleration-sensitive switch is preferably uniaxial. When connected in a circuit, the switch closes and therefore generates a pulse only when accelerated in a predetermined direction or in a direction within 90 degrees of the predetermined direction. As a further requirement of when a pulse is generated, a vector component of acceleration in the predetermined direction must exceed a particular magnitude for a pulse to be generated. If this vector component fails to reach the particular magnitude (which will occur if, for example, the direction of acceleration is 90 degrees or more from the predetermined direction), the switch will not close and generate a pulse. If a pulse is generated, the pulse lasts only as long as the switch continues to be accelerated with the vector component having the particular magnitude, thus maintaining the switch closed.

The particular magnitude to which the acceleration-sensitive switch responds, is chosen based on the characteristics of the human motion to be counted. For human motions which result in high accelerations in the predetermined direction, this magnitude can be set at a high value. Conversely, when the human motion results in lower levels of acceleration, the particular magnitude is set at a lower level.

The computer is responsive to pulses from the acceleration-sensitive switch and therefore can determine when the device is being accelerated with sufficient magnitude in the predetermined direction. In addition, the computer is programmed to measure or time the duration of the pulses received from the acceleration-sensitive switch, and is further programmed with parameters indicative of the minimum and maximum duration of such a pulse which will be deemed to have resulted from the occurrence of the human motion worthy of being counted. By programming the computer in this manner, the computer can readily determine when the human motion has occurred.

The computer is further programmed to count the number of pulses which have exceeded the minimum duration but have not exceeded the maximum duration, and to generate an output signal indicative of this count. The output signal from the computer therefore represents the number of times the human motion has occurred.

Preferably, the computer is also programmed to ignore any pulses from the acceleration-sensitive switch which occur within a predetermined time period after detection of a previous pulse. The predetermined time period is preferably chosen based on the expected minimum time period between occurrences of the human motion. By programming the computer in this manner, a single occurrence of the human motion will not trigger more than one count. After the predetermined time period has expired, the computer resumes its detection and counting of pulses.

The display receives the output signal from the computer and responds by visually displaying the count. In order to reset the count, a reset switch is provided. The reset switch is connected to the computer and can be manually activated to reset the computer's count to zero.

The above and other objects and advantages will become more readily apparent when reference is made to the following description taken in conjunction with the accompanying drawings.

DETAILED DESCRIPTION OF THE PREFERRED EMBODIMENTS

A preferred embodiment of the present invention will now be described with reference first to FIGS. 1 and 2.

Figure 1:
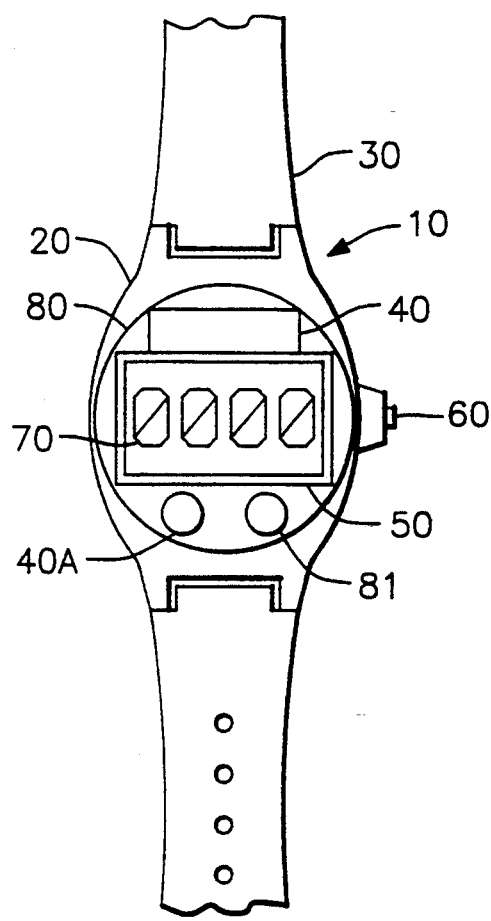
FIG. 1 is a top view of a preferred embodiment of the inventive device for detecting and counting occurrences of specific human motions.
Figure 2:
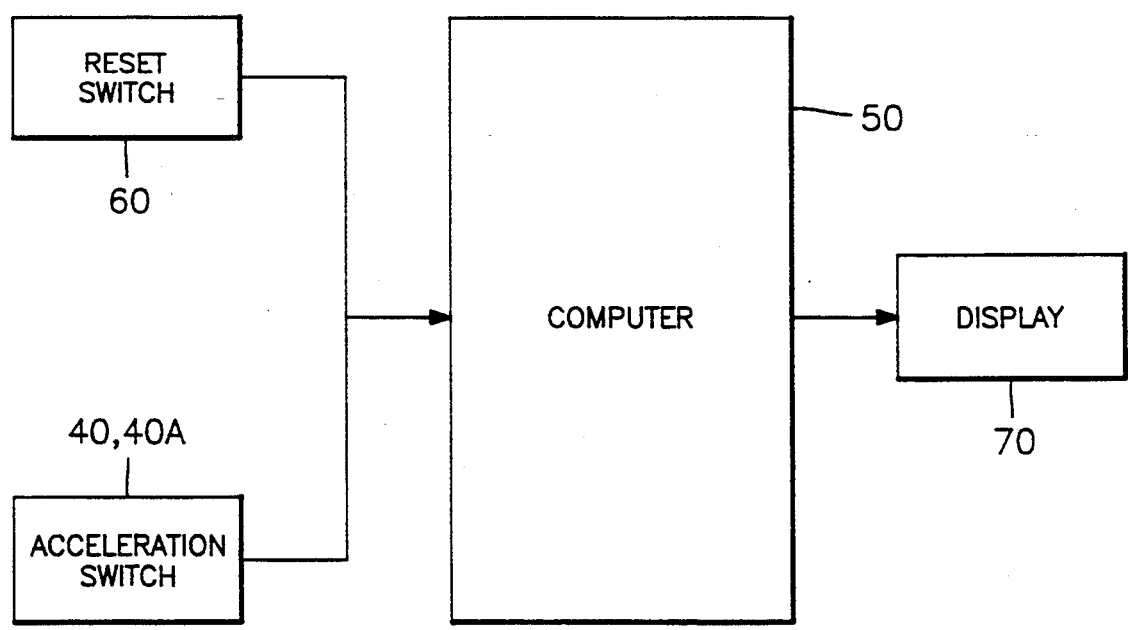
FIG. 2 is a block diagram of the inventive device illustrated in FIG. 1.

The preferred embodiment shown in FIGS. 1 and 2 comprises a device 10 for detecting and counting occurrences of specific human motions. The device 10 includes a watch-like housing 20, and a strap 30 for mounting the device 10 to a part of the human body which takes part in the motion. The strap 30, for example, can engage a wrist or hand, or alternatively, engages an extension of the human body such as a fishing rod. Mounting means other than the strap 30 can be used, such as VELCRO ® which secures the device 10 to the outer surface of a glove.

The device 10 further comprises an acceleration-sensitive switch 40 or 40A; a computer 50 connected to an output from the acceleration-sensitive switch 40 or 40A; a reset switch 60 connected to the computer 50; and a display 70 which is controlled by the computer 50. Although FIG. 1 shows both acceleration-sensitive switches 40 and 40A, it is understood that the commercial embodiments will include one of the switches 40 or 40A, depending on the type of motion to be detected and counted. Likewise, it is understood that non-digital circuitry and/or discrete integrated circuit components can be substituted in place of computer 50 to perform the functionality thereof, without departing from the spirit and scope of the present invention.

The acceleration-sensitive switch 40 or 40A is preferably one of many commercially available inertia switches. These inertia switches, for example, include an internal mass connected to a spring in such a manner that the mass moves against the spring when subjected to acceleration in a predetermined direction. When the acceleration exceeds a certain threshold, the mass displaces the spring sufficiently to complete an electrically conductive path between two terminals of the switch. By connecting these two terminals in an electrical circuit to a power supply (via various resistor networks), the switch creates an electrical pulse when it closes, i.e. when the contacts physically touch each other. Though inertia switches in an electrical circuit constitute the preferred arrangement, it is understood that other similar switches and switching arrangements will suffice.

The acceleration-sensitive switch 40 or 40A is preferably uniaxial. The switch closes and generates a pulse only when accelerated in a predetermined direction (the direction of its aligned "axis") or in a direction within 90 degrees of the predetermined direction. In addition, a vector component V of acceleration lying in the predetermined direction must exceed a particular magnitude M for a pulse to be generated by the switch 40 or 40A. If this vector component V fails to reach the particular magnitude M (which will occur if, for example, the direction of acceleration is 90 degrees or more from the predetermined direction or the magnitude of acceleration is too small), the switch 40 or 40A will not generate a pulse. If a pulse is generated, the pulse lasts only as long as the switch 40 or 40A continues to be accelerated and thus closed with the vector component V being at least as great as the particular magnitude M.

The particular magnitude M to which the acceleration-sensitive switch 40 or 40A responds, is chosen based on the characteristics of the human motion to be counted. For human motions which result in high accelerations in the predetermined direction, this magnitude M can be set at a high value. Conversely, when the human motion results in lower levels of acceleration, the particular magnitude M is set at a lower value.

The computer 50 receives the pulses from the acceleration-sensitive switch 40 or 40A and therefore can determine when the device 10 is being accelerated with sufficient magnitude in the predetermined direction. In addition, the computer 50 is programmed to measure or time the duration of the pulses received from the acceleration-sensitive switch 40 or 40A, and is further programmed with parameters indicative of the minimum and maximum durations ($t_{min}$ and $t_{max}$) of such a pulse which will be deemed to have resulted from the occurrence of the human motion. By programming the computer 50 in this manner, the computer 50 can readily determine when the human motion worthy of being counted has occurred.

The computer 50 is further programmed to count the number of pulses which have exceeded the minimum duration $t_{min}$ but not the maximum duration $t_{max}$, and to generate an output signal indicative of this count. This output signal from the computer 50 therefore represents the number of times the human motion has occurred.

Preferably, the computer 50 is also programmed to ignore any pulses from the acceleration-sensitive switch 40 or 40A which occur within a predetermined time period T after detection of a previous pulse. The predetermined time period T is chosen based on the expected minimum time interval between occurrences of the motion. By programming the computer 50 in this manner, a single occurrence of the human motion will not trigger more than one count. After the predetermined time period T has elapsed, the computer 50 resumes its detection and counting of pulses.

The display 70 receives the output signal from the computer 50 and responds by visually displaying the count. In order to reset this count, the reset switch 60 is provided. The reset switch 60 is connected to the computer 50 and can be manually activated to reset the computer's count to zero.

The reset switch 60; the computer 50; and the acceleration-sensitive switch 40 or 40A are preferably mounted to a PC board 80 which, in turn, is secured to the housing 20. The entire device 10 is preferably powered by a battery 81 which is also mounted to the PC board 80.

The device 10 can be used in a variety of contexts, and the actual orientation of the acceleration-sensitive switch 40 or 40A depends on the intended use of the device 10. Preferably, the switch 40 or 40A is oriented so that the predetermined direction associated with the switch's operation is aligned with a centripetal force vector of the human motion to be counted. Alignment with the centripetal force vector is preferred because it minimizes the likelihood that random motions will trigger the switch 40 or 40A.

Alternatively, when the centripetal force generated by the human motion is insufficient, the switch 40 or 40A can be oriented so that the predetermined direction is aligned with the vector of maximum linear acceleration created by the human motion.

Figure 3:
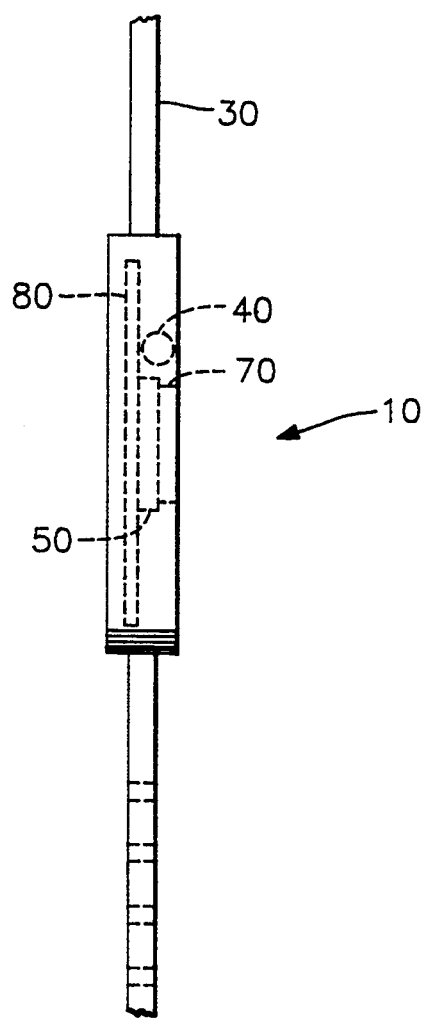
FIG. 3 is a side view of one preferred embodiment of the present invention.

FIG. 3 illustrates the device 10 having switch 40 mounted on the PC board 80. Switch 40 lies substantially flat on the PC board 80. As will become more apparent hereinafter, switch 40 is oriented on the PC board 80 so that when the device 10 is mounted on the wrist of a user, the axis of the switch 40 is substantially aligned with the axis of a straightened arm, from the elbow to the fingers. Moreover, the contacts in switch 40 close at the end of the body of the switch closest to the fingers, when the device is mounted on the wrist of a user (FIG. 6).

Figure 4:
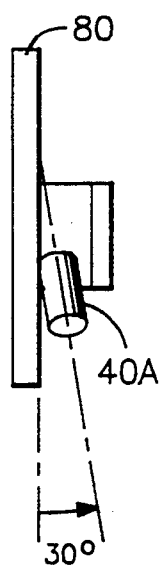
FIG. 4 is a side view of the internal electronics in accordance with another preferred embodiment.
Figure 5:
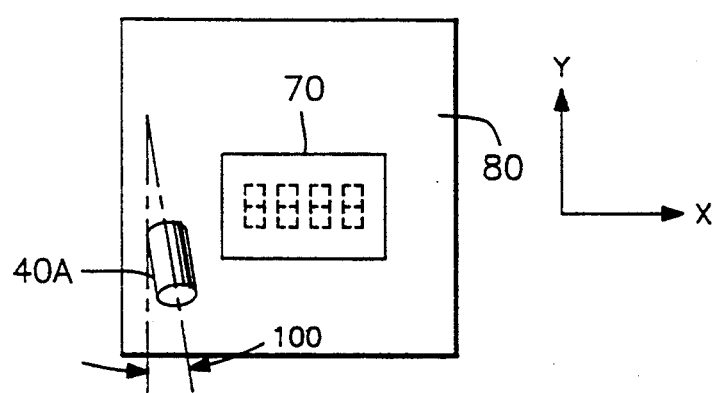
FIG. 5 is a top view of the circuit board supporting the electronics shown in FIG. 4.

By contrast, as shown in FIG. 4 and 5, switch 40A is mounted 30° off the plane of the PC board 80 and at a 10° yaw angle relative to the y-axis, shown in FIG. 5. The contacts of switch 40A close at the end of the body of the switch furthest from the circuit board.

Figure 6:
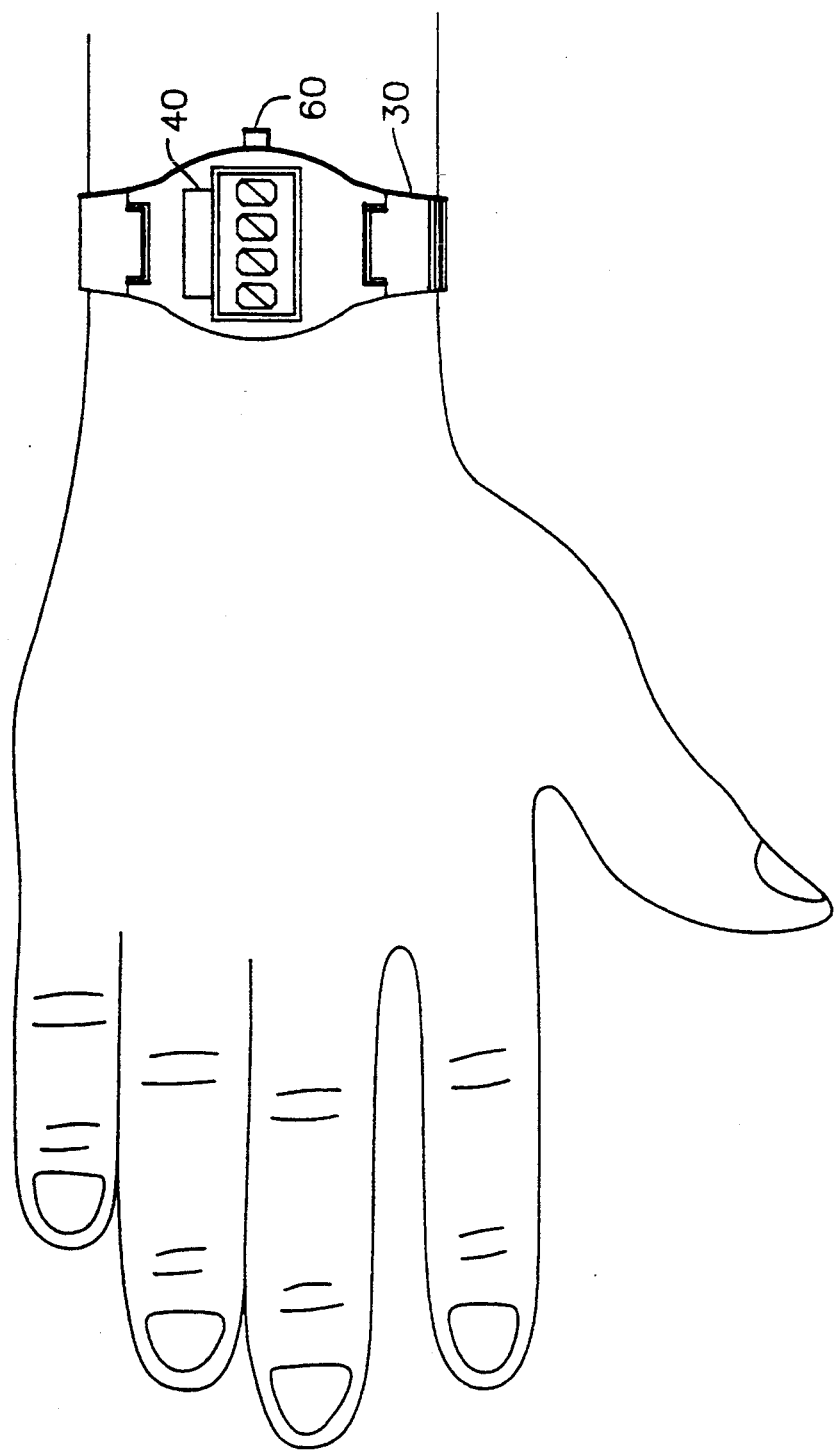
FIG. 6 is a top partial view illustrating the mounting of the device of FIG. 3 on the wrist of a user.
Figure 7:
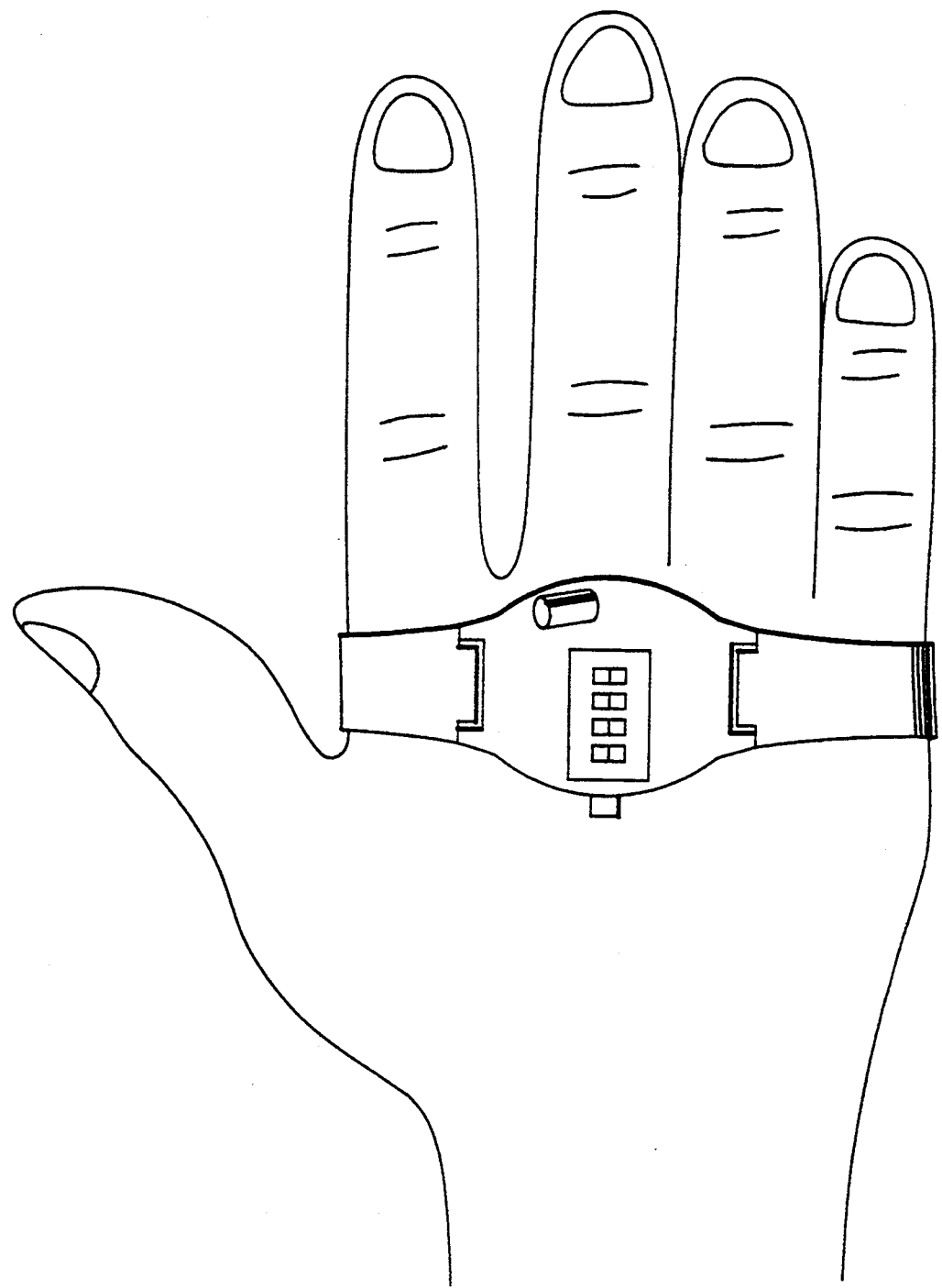
FIG. 7 is a top view illustrating the mounting of the device of FIGS. 4 and 5 on the back of the hand of the user.

FIG. 6 illustrates the mounting of the device for counting pitches thrown. The device 10 is secured to the throwing arm in the same way that a wrist-watch is typically secured. As shown, the switch 40 is mounted to the PC board 80 and the device attached to the wrist so that the predetermined direction associated with the switch 40 is aligned with the major bones of the forearm. The centripetal force generated by a throwing motion, therefore, acts towards the elbow of the arm. In addition, the sensitivity of the switch 40 is chosen such that whenever a pitch is thrown, the switch 40 undergoes sufficient centripetal acceleration to exceed the magnitude M and produce an output pulse. The computer 50 (which receives the output pulse) is programmed with the minimum and maximum durations $t_{min}$ and $t_{max}$ of a pulse which will be deemed to have resulted from a thrown pitch. The computer 50 is also programmed to ignore pulses which occur within a time period T after detecting a previous pulse. The time period T preferably corresponds to an expected minimum period of time that elapses between pitches. By using the foregoing arrangement, the device 10 of the present invention is able to count and display the number of pitches thrown irrespective of whether the pitches are thrown underhand or overhand.

For counting the number of times a fishing line is cast, the device 10 is preferably secured to the back of the casting hand, so that the PC board 80 remains parallel to the back of the hand. The user then grasps the fishing rod normally between thumb and first finger, to make a cast, whereby the hand when cocked, faces almost directly upwards over the right shoulder (if a right-handed caster) and when the casting motion is complete, the palm faces nearly directly downwards. This arrangement is preferred because most of the motion involved in casting involves forward flipping motion of the wrist that occurs distally with respect to the wrist. However, by offsetting the switch 40A from the PC board 80, false triggering from normal arm swaying accompanying walking will not occur. In fact, the angle between the predetermined direction associated with the switch 40A, and the PC board 80 is chosen so that the predetermined direction aligns with the direction of maximum linear acceleration in a casting motion. Linear acceleration forces generated by the casting motion, therefore, act along the aligned predetermined direction of the switch 40A. In addition, the sensitivity of the switch 40A is chosen such that whenever a casting motion is made, the switch 40A undergoes sufficient linear acceleration to exceed the magnitude M and produce an output pulse. The computer 50 (which receives the output pulse) is programmed with the minimum and maximum durations $t_{min}$ and $t_{max}$ of a pulse which will be deemed to have resulted from a casting motion. In addition, the computer 50 is programmed to ignore pulses which occur within a time period T after detecting a previous pulse. The time period T preferably corresponds to an expected minimum period of time that elapses between successive casts of the fishing line. By using the foregoing arrangement, the device 10 of the present invention is able to count and display the number of times a casting motion occurs.

Returning briefly to FIG. 2, the acceleration-sensitive switch and the reset switch provide the only inputs to the computer 50. The parameters $t_{min}$, $t_{max}$, and T, for different applications of the device 10, are stored in a memory of the computer 50.

Figure 8:
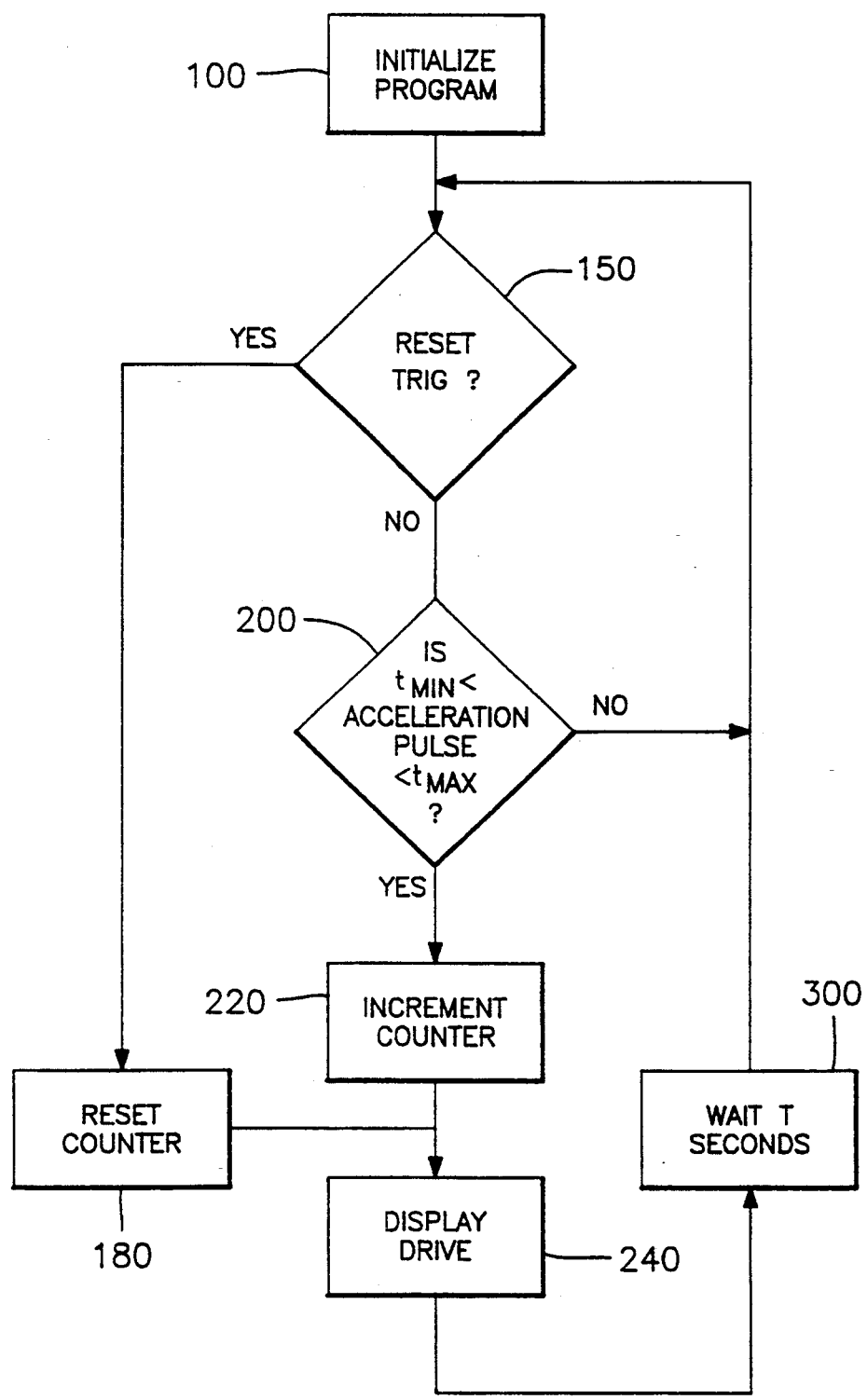
FIG. 8 is a flow chart illustrating the processing steps implemented by the inventive device to count occurrences of specific human motions.

Turning now to the flow chart of FIG. 8, the computer 50 is programmed to execute a method for detecting and counting occurrences of a specific human motion. In step 100 of the method, the computer 50 is initialized with a computer program to carry out the instant method, and with parameters ($t_{min}$, $t_{max}$ and T) corresponding to the desired use of the device 10.

In step 150, the computer 50 periodically scans the input from the reset switch 60 to determine whether the switch 60 has been activated. If the reset switch 60 has been activated, the computer executes step 180 and resets an internal counter to zero.

If in step 150 the reset switch 60 has not been activated, the computer 50 then scans, in step 200, the input from the acceleration-sensitive switch to determine whether a pulse has been transmitted. If a pulse is detected by the computer 50, the computer 50 determines whether the pulse's duration exceeds the minimum duration $t_{min}$ but not the maximum duration $t_{max}$. If the pulse's duration fails to exceed the minimum duration $t_{min}$ or does exceed the maximum duration $t_{max}$, the computer 50 again executes step 150. However, if the duration of the pulse falls between the minimum duration $t_{min}$ and the maximum duration $t_{max}$, the internal counter is incremented in step 220.

After step 220 and also after step 180, the display 70 is driven by the computer 50 or a display driver, in step 240, to display the count currently in the internal counter.

After execution of step 240, the computer 50 waits until expiration of the time period T before returning to step 150.

By programming the computer 50 to execute the foregoing method, the device 10 can automatically detect and count occurrences of a specific human motion.

A preferred computer 50 for use with the present invention is the PC 16CSS manufactured by Microchip.

The device 10 can also be built using chips such as the 14990 debouncer and detector manufactured by Motorola and the 74122 one-shot manufactured by Texas Instruments, which together can detect and time the pulses. The output from the 74122 would be used to drive any commonly available display and/or counter module. In a large production scenario, it is understood that custom designed chips may be used to reduce manufacturing costs. Still other similar computers or microprocessor chips will suffice.

When counting pitches, a preferred value for the minimum duration $t_{min}$ is set between 0.170 seconds and 0.190 seconds (preferably at 0.180 seconds), while a preferred value for the maximum duration $t_{max}$ is set between 0.9 seconds and 1.1 seconds (preferably at 1.0 second). Preferred values for the time period T range between 3 and 5 seconds, and is preferably set at 4 seconds. By setting the parameters at the foregoing values, the device is capable of accurately counting pitches thrown as slow as twenty miles per hour, and as fast as ninety miles per hour.

When counting casts of a fishing line, a preferred value for the minimum duration $t_{min}$ stored in the computer 50 is 0.020–0.030 seconds (preferably set at 0.025 seconds), while a preferred value for the maximum duration $t_{max}$ is set between 0.17 seconds and 0.19 seconds (preferably at 0.18 seconds). A preferred value for the time period T used in counting casts also ranges between 3 and 5 seconds, and is preferably set at 4 seconds.

Although the foregoing description mentions use of an internal counter, it is understood that the counter can be provided as a separate component. Likewise, a separate memory can be provided for the computer 50.

For counting the number of pitches thrown, the acceleration-sensitive switch 40 preferably responds to an acceleration magnitude M of 2.8 G to 3.2 G (preferably 3.0 G) along the predetermined direction. When counting casts of a fishing line, the acceleration-sensitive switch 40A preferably responds to an acceleration magnitude M of 1.0 G to 1.4 G (preferably 1.2 G) directed along the predetermined direction.

The present invention can also comprise a separate display driver connected between the computer 50 and the display 70, to thereby assist the computer 50 in driving the display 70.

It is also understood that the computer 50 need not be programmed to use the maximum duration parameter $t_{max}$, especially when the particular magnitude to which the switch 40 or 40A responds is greater than 1.5 G, such as counting pitching motions where the total forces acting on the switch is in the range of 4 G. When the particular magnitude is less than 1.5 G, the maximum duration $t_{max}$ is useful in preventing inadvertent triggering of the switch 40 or 40A in response to long random motions.

Though the present invention has been described with reference to the preferred embodiments, it is understood that the invention is not limited to these embodiments. For example, the electronics of the device 10 may be incorporated in a digital wrist-watch to thereby provide a time of day indication in addition to providing the counting function described herein. In addition, the electronics of the device 10 could be incorporated within the body of a fishing poll or other motion devices such as a tennis racket. The present invention is therefore limited only by the scope of the appended claims.

We claim:

1. A device for detecting and counting occurrences of a specific motion, said device comprising:
   at least one acceleration-sensitive switch;
   processing means connected to an output of said at least one acceleration-sensitive switch, for determining based on the output from said at least one acceleration-sensitive switch whether said specific motion has occurred and having means for counting occurrences of said specific motion; and
   display means controlled by the processing means to display results from said means for counting, said results being indicative of the number of times the specific motion has occurred;
   wherein said at least one acceleration-sensitive switch is uniaxial and closes in response to acceleration forces greater than a predetermined magnitude in a predetermined direction corresponding to an axis of the switch, and
   wherein the switch outputs a pulse when closing, the duration of the pulse depending on the amount of time that acceleration forces in the predetermined direction exceed the predetermined magnitude.

2. The device of claim 1, wherein said processing means is programmed to compare the duration of said pulse with a minimum duration $t_{min}$ beyond which said pulse will be deemed to have resulted from the occurrence of said specific motion.

3. The device of claim 2, wherein said means for counting is incremented only when the duration of a pulse from said at least one acceleration-sensitive switch exceeds said minimum duration $t_{min}$.

4. The device of claim 2, wherein said means for counting is not responsive to pulses which occur within a predetermined time period T after detection of a previous pulse.

5. The device of claim 4, wherein said processing means further comprises a memory for storing parameter values for the minimum duration $t_{min}$ and predetermined time period T.

6. The device of claim 1, wherein said processing means is programmed to compare the duration of said pulse with a minimum duration $t_{min}$ and a maximum duration $t_{max}$ between which said pulse will be deemed to have resulted from the occurrence of said specific motion.

7. The device of claim 6, wherein said means for counting is incremented only when the duration of a pulse from said at least one acceleration-sensitive switch falls between said minimum duration $t_{min}$ and said maximum duration $t_{max}$.

8. The device of claim 6, wherein said means for counting is not responsive to pulses which occur within a predetermined time period T after detection of a previous pulse.

9. The device of claim 8, wherein said processing means further comprises a memory, for storing parameter values for the minimum duration $t_{min}$, the maximum duration $t_{max}$ and the predetermined time period T.

10. A device for detecting and counting occurrences of a specific motion, said device comprising:
    a housing;
    an acceleration-responsive switch which closes in response to acceleration forces greater than a predetermined magnitude in a predetermined direction;
    means for mounting the acceleration-responsive switch in said housing in an orientation so as to make the acceleration-responsive switch responsive to acceleration forces in a direction indicative of the motion to be detected and counted, and non-responsive to substantially all other motions; and processing means connected to a circuit arrangement with said acceleration-responsive switch to receive an output of said acceleration-responsive switch, said processing means determining based on the output of the acceleration-responsive switch whether a specific motion has occurred and including means for counting occurrences of the specific motion, wherein the acceleration-responsive switch has a major axis and closes in response to acceleration forces greater than the predetermined magnitude in the direction of the major axis, and wherein the acceleration-responsive switch outputs a pulse when closing, the duration of the pulse depending on the amount of time that acceleration forces in the direction of the major axis exceed the predetermined magnitude.

* * * * *